United States Patent [19]

Swedlow et al.

[11] Patent Number: 5,226,417
[45] Date of Patent: Jul. 13, 1993

[54] APPARATUS FOR THE DETECTION OF MOTION TRANSIENTS

[75] Inventors: David B. Swedlow, Foster City; Robert L. Clark, Hayward; Adnan I. Merchant, Fremont; Deborah A. Briggs, San Ramon; Jessica A. Warring, Millbrae, all of Calif.

[73] Assignee: Nellcor, Inc., Hayward, Calif.

[21] Appl. No.: 667,152

[22] Filed: Mar. 11, 1991

[51] Int. Cl.[5] ............................................. A61B 5/00
[52] U.S. Cl. ..................................... 128/633; 356/41
[58] Field of Search ............... 128/633, 664, 665, 670, 128/677, 682; 356/40, 41

[56] References Cited

U.S. PATENT DOCUMENTS

| B1 4,653,498 | 4/1989 | New, Jr. |
| 4,802,486 | 2/1989 | Goodman |
| 4,830,014 | 5/1989 | Goodman |
| 4,869,254 | 9/1989 | Stone |
| 4,911,167 | 3/1990 | Corenman |
| 5,025,791 | 6/1991 | Niwa |
| 5,099,702 | 3/1992 | French .............................. 73/862.68 |

OTHER PUBLICATIONS

Nellcor pamphlet "Nellcor redefines pulse oximetry. Introducing the Nellcor N-200 with ECG synchronization".
Nellcor pamphlet "N-200. Nellcor N-200 pulse oximeter with C-LOCK ECG synchronization".
"C-LOCK ECG Synchronization Principles of Operation", Pulse Oximetry Note Number 6, Reference Note, Nellcor Inc., 1988.

Primary Examiner—Lee S. Cohen
Assistant Examiner—Kevin Pontius
Attorney, Agent, or Firm—Townsend and Townsend Khourie and Crew

[57] ABSTRACT

An apparatus for detecting movement in patients coupled to pulse oximeters and a method for using the signal generated by the apparatus to filter out the effects of motion from the test results generated by the pulse oximeter are disclosed. In a preferred embodiment, a piezoelectric film located in close proximity to the pulse oximeter's sensor provides a voltage signal whenever movement occurs near the sensor. This voltage signal is processed and the resulting signal is used to correct the oximeter's measurements. In addition to piezoelectric film, accelerometers and strain gauges are also usable to provide a signal indicative of motion.

6 Claims, 3 Drawing Sheets

5,226,417

APPARATUS FOR THE DETECTION OF MOTION TRANSIENTS

BACKGROUND OF THE INVENTION

This invention relates generally to non-invasive pulse monitors such as pulse oximeters. In particular, it relates to the detection of motion transients and the filtering of these transients from the blood oxygen signals sent to the pulse oximeter.

Photoelectric pulse oximetry is known. Pulse oximeters typically measure and display various blood flow characteristics including the blood oxygen saturation of hemoglobin in arterial blood, the volume of individual blood pulsations supplying the flesh, and the rate of blood pulsations corresponding to each heartbeat of the patient. The oximeters pass light through body tissue in a location where blood perfuses the tissue (i.e. a finger or an ear) and photoelectrically sense the absorption of light in the tissue. The amount of light absorbed is then used to calculate the amount of the blood constituent being measured.

Several different wavelengths of light are simultaneously or nearly simultaneously transmitted through the body tissue. These wavelengths are selected based on their absorption by the blood components being measured. The amount of transmitted light passing through the tissue will vary in accordance with the changing amount of blood constituent in the tissue.

An example of a commercially available pulse oximeter is the Nellcor Incorporated Pulse Oximeter model N-200 (herein "N-200"). The N-200 is a microprocessor controlled device that measures oxygen saturation of hemoglobin using light from two light emitting diodes ("LEDs"), one having a discrete frequency of about 660 nanometers in the red light range and the other having a discrete frequency of about 925 nanometers in the infrared range. The N-200's microprocessor uses a four-state clock to provide a bipolar drive current for the two LEDs so that a positive current pulse drives the infrared LED and a negative current pulse drives the red LED. This illuminates the two LEDs alternately so that the transmitted light can be detected by a single photodetector. The clock uses a high strobing rate, roughly 1,500 Hz, and is consequently easy to distinguish from other light sources. The photodetector current changes in response to the red and infrared light transmitted and is converted to a voltage signal, amplified and separated by a two-channel synchronous detector—one channel for processing the red light wave form and the other channel for processing the infrared light waveform. The separated signals are filtered to remove the strobing frequency, electrical noise and ambient noise and then digitized by an analog to digital converter ("ADC"). As used herein, incident light and transmitted light refers to light generated by the LEDs or other light sources, as distinguished from ambient or environmental light.

The light source intensity can be adjusted to accommodate variations in patients' skin color, flesh thickness, hair, blood, and other variants. The light transmitted is thus modulated by the absorption of light in the blood pulse, particularly the arterial blood pulse or pulsatile component. The modulated light signal is referred to as the plethysmograph waveform, or the optical signal. The digital representation of the optical signal is referred to as the digital optical signal. The portion of the digital optical signal that refers to the pulsatile component is called the optical pulse.

The detected digital optical signal is processed by the microprocessor of the N-200 to analyze and identify arterial pulses and to develop saturation. The microprocessor decides whether or not to accept a detected pulse as corresponding to an arterial pulse by comparing the detected pulse against the pulse history. To be accepted, a detected pule must meet certain predetermined criteria, including the expected size of the pulse, when the pulse is expected to occur, and the expected ratio of the red light to infrared light in the detected optical pulse. Identified individual optical pulses accepted for processing are used to compute the oxygen saturation from the ratio of maximum and minimum pulse levels as seen by the infrared wavelength.

A problem with pulse oximeters is that the plethysmograph signal and the optically derived pulse rate may be subject to irregular variants in the blood flow that interfere with the detection of the blood flow characteristics. For example, when a patient moves, inertia may cause a slight change in the venous blood volume at the sensor site. This, in turn, alters the amount of light transmitted through the blood and the resetting optical pulse signal. These spurious pulses, called motion artifacts, may cause the oximeter to process the artifact waveform and provide erroneous data.

It is well known that electrical heart activity occurs simultaneously with the heartbeat and can be monitored externally and characterized by an electrocardiogram ('ECG') waveform. The ECG waveform comprises a complex waveform having several components that correspond to electrical heart activity. A QRS component relates to ventricular heart contraction. The R wave portion of the QRS component is typically the steepest wave therein, having the largest amplitude and slope, and may be used for indicating the onset of cardiovascular activity. The arterial blood pulse flows mechanically and its appearance in any part of the body typically follows the R wave of the electrical heart activity by a determinable period of time that remains essentially constant for a given patient.

One method to reduce or eliminate the effects of motion artifacts is to synchronize the ECG signal and the optical pulse signal and process the two signals to form a composite signal. This composite signal is then used to measure the level of oxygen saturation. This method is called ECG synchronization.

In the first stage of synchronization, the optical pulse signal is filtered to minimize the effects of electronic high frequency noise, using a low pass filter. Next, the oximeter positions the newly acquired optical pulse in memory, using the QRS complex as a reference point for aligning sequential signals. In other words, when the QRS complex occurs, the oximeter begins processing the optical pulse data.

In the third stage, the new optical pulse signal is combined with the composite of the signals that were previously stored in the memory. Signals are combined using an adjustable weighted algorithm wherein, when the new composite signal is calculated, the existing memory contents are weighted more heavily than the new optical signal pulse.

Finally, the oxygen saturation level is measured from the composite signal. This determinaton is on the ratios of the maximum and minimum transmission of red and infrared light. As each sequential QRS complex and optical pulse signal are acquired, the process of filtering, positioning, combining and measuring saturation is repeated. As aperiodic signals such as motion artifacts will not occur synchronously on the ECG and the detected optical pulse, the effect of these aperiodic signals is rapidly attenuated.

Another method to detect and reduce the effect of motion artifacts involves correlating the occurrence of cardiovascular activity with the detection of arterial pulses by measuring the ECG signal, detecting the occurrence of the R-wave portion of the ECG signal, determining the time delay by which an optical pulse in the detected optical signal follows the R-wave, and using the determined time delay between the R-wave and the following optical pulse to evaluate arterial blood flow only when it is likely to represent a true blood pulse. The measured time delay is used to determine a time window when, following the occurrence of an R-wave, the probability of finding an optical pulse corresponding to a true arterial pulse is high. The time window provides an additional criterion to be used in accepting or rejecting a detected pulse as an optical pulse. Any spurious pulses caused by motion artifacts or noise occurring outside of the correct time window are typically rejected and are not used to calculate the amount of blood constituent. Correlating the ECG with the detached optical pulses thus provides for more reliable measurement of oxygen saturation.

Other methods to detect and eliminate the effects of patient motion have been developed. A time-measure of the detected optical signal waveform containing a plurality of periodic information corresponding to arterial pulses caused by the patient's heartbeat and periodic information unrelated to pulsatile flow is collected, and the collected time measure of information is processed to obtain enhanced periodic information that is closely related to the most recent arterial pulsatile blood flow. The time-measure may comprise a continuous portion of detected optical signals including a plurality of periodic information from successive heartbeats, or a plurality of discrete portions of detected optical signals including a corresponding plurality of periodic information.

By updating the time-measure of information to include the most recently detected aperiodic information, and processing the updated measure collectively, an updated enhanced periodic information is obtained (including the new and historical data) from which aperiodic information (including any new aperiodic information) is attenuated. In some embodiments, the updating process includes subtracting detected signals older than a certain relative time from the collected time-measure. By collectively processing a time-measure including successive periodic information to obtain the enhanced periodic information, and using the enhanced periodic information as the basis for making oxygen saturation calculations, the accuracy and reliability of oxygen saturation determinations can be significantly increased. The time-means may be collectively processed in either the time domain or the frequency domain.

By synchronizing the occurrence of successive R-waves, it becomes possible to add the corresponding successive portions of the detected optical signal together so that the periodic information (optical pulses) corresponding to the arterial pulse in each portion will add in phase. The weighted magnitude of the new periodic information is reinforced by the existence of the weighted enhanced periodic information at the same time location in accordance with the degree of synchrony. If the new optical pulse is identical to the composite pulse then the updated result is a composite optical pulse having the same magnitude. If the magnitudes differ, the additive result will differ according to the relative weights.

As a result of the collected, synchronized additive process, any aperiodic information that may be present in the portions of the detected optical signals are also weighted and added to the weighted composite portion waveform. However, because aperiodic signals differ in pulse shape, duration, height, and relative time of occurrence within each portion, and are not synchronous with heart activity, they do not add in phase. Rather, they add in a cancelling manner whereby their weighted sum is spread across the relative time frame of the composite portion.

By processing portions including the periodic information collectively, aperiodic information is attenuated by the absence of any corresponding historical aperiodic signal in the prior composite portion or any subsequent aperiodic signal at that relative time following heart activity. As the new information can be given a small weight compared to the absolute weight given the prior composite, new aperiodic information is quickly and effectively attenuated and filtered out of the resultant additive portions.

Although all of the described methods improve the quality of the pulse oximeter's measurements by reducing the effects of motion transients and other spurious signals, they provide no independent indication that motion has occurred. Such an independent verification of patient motion is useful for pulse oximetry. In certain cases, it is also possible that an ECG signal will not be available. In these cases, having an independent motion detection capability would be essential to detect motion artifacts.

SUMMARY OF THE INVENTION

A preferred embodiment of the present invention comprises a method and apparatus for minimizing the effect of motion artifacts in pulse oximetry. Unlike known methods, the present invention derives a motion detection signal independently of the pulse signal. Although the present invention will be described relative to its use in pulse oximetry, its usefulness is not limited to that area alone.

A preferred embodiment of the present invention will be described in connection with an adhesive finger sensor for use with a pulse oximeter. Other sensors may be used, however, without departing from the scope of the invention.

In an adhesive finger sensor for a pulse oximeter, a strip of piezoelectric film has been incorporated. The film covers the nearest movable joint to the sensor; in this example, the joint on the finger to which the sensor is attached. The change of strain on the motion sensing element caused by moving the finger to which the sensor is attached generates a charge within the element, as in a capacitor. A gain resistor mounted across the motion sensing element bleeds off the charge, thereby creating a voltage signal that is proportional to the rate of bending.

By properly processing this voltage signal, motion artifacts can be detected and their effect on the calculation of blood oxygen compensated for.

The invention will now be described in detail, with reference to the figures tested and described below.

DESCRIPTION OF THE SPECIFIC EMBODIMENT(S)

Figure 1:
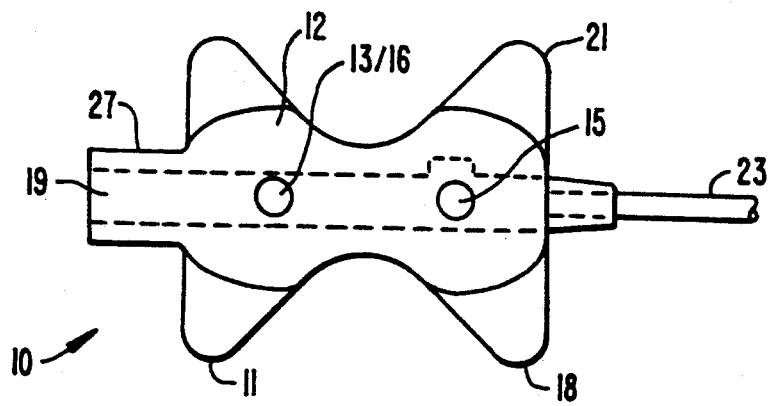
FIG. 1 shows an assembled sensor according to the present invention.
Figure 2:
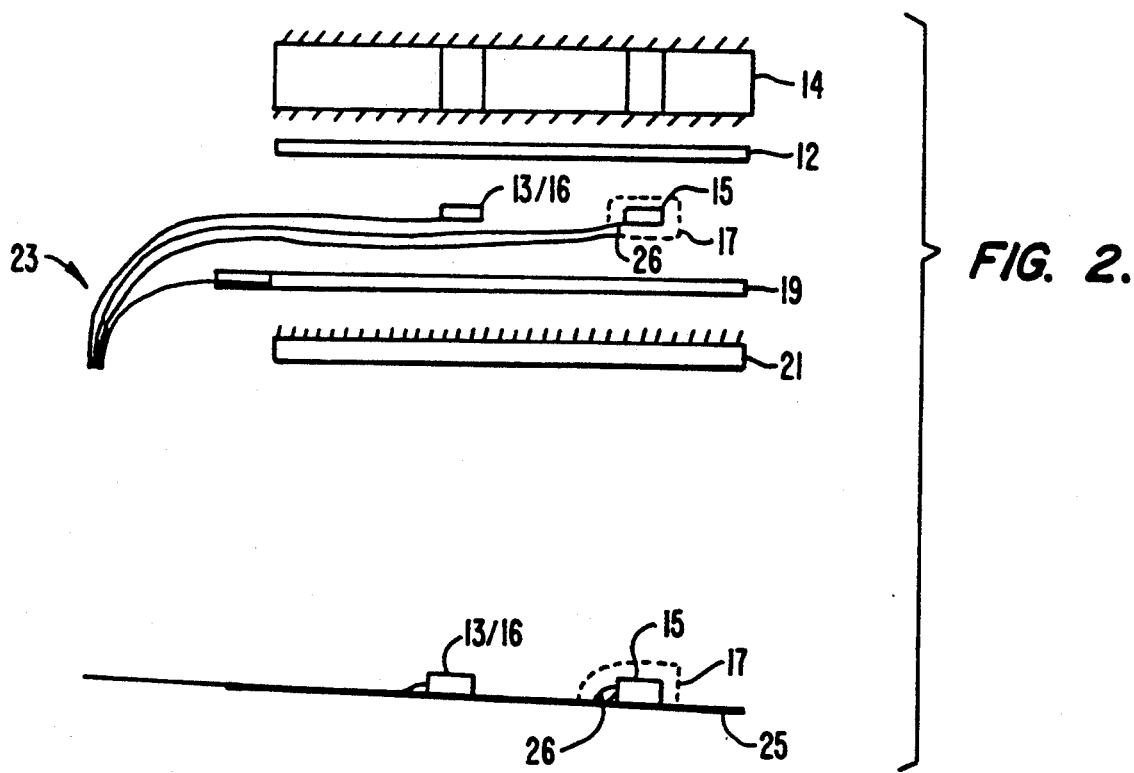
FIG. 2 is a cross-section of the sensor shown in FIG. 1.

A preferred embodiment of the motion detection sensor of the present invention is shown in FIGS. 1 and 2. Sensor package 10, which includes light-emitting diodes 13 and 16 and photodetector 15, is for transillumination of a blood perfused portion of flesh to measure light extinction during transillumination. The sensor is preferably mounted on a fingertip but any digit or other blood perfused tissue will work. The sensor conforms to and with the cutaneous layer of the blood perfused portion of flesh upon which the sensor is placed. A first end 11 of sensor 10 is disposed on one side of the flesh to be transilluminated and a second end 18 is disposed on the opposite and opposed side of the flesh to be transilluminated.

When the sensor is adhesively fastened, the effect of the light source and photodetector being integrated into the adhesive fastener is that they become, in effect, a part of the skin. The resulting device is resistant to accidental removal and avoids constriction of blood vessels. Most importantly, the low mass of the sensor itself and its conformance to the skin prevents motion and the possible resulting contact interruption between the light source, photodetector and flesh.

In the present invention, as illustrated in FIGS. 1 and 2, the dimensions of the butterfly-shaped bandage containing the sensor are such that the butterfly "wings" (ends 11 and 18) do not extend beyond the first joint of the patient's finger when the sensor is attached to a patient. Bandage layer 21 is preferably an adhesive cotton elastic material which completely covers opaque white polypropylene layer 14. Holes are formed in opaque, adhesive coated polypropylene layer 14 for the optical components. A clear, double-coated 0.003 thick polyethylene layer 12 covers these holes.

The LEDs 13 and 16, as well as photodetector 15 are placed beneath layer 12. Photodetector 15 is mounted on lead frame package 26 and is surrounded by Faraday shield 17. The LEDs, photodetector and Faraday shield are all coupled to the pulse oximeter by means of leads running through cable 23. LEDs 13/16 are commercially available and are mounted in a lead frame package 29. The red wavelength LED generates at least 0.85 milliwatts and the I.R. LED generates 1.45 milliwatts of power. In an alternate embodiment, the lead frame packages 26 and 29, photodetector 15 and LEDs 13 and 16 are mounted on a flexible substrate 25. In the preferred embodiment, opaque layer 14 and clear layer 12 are peanut-shaped to provide adequate coverage of the optical components, wires and motion sensor. The peanut shape also provides sufficient surface area to adhere to the butterfly without subsequent delamination and minimizes assembly time.

Motion sensing element 19 is a strip of piezoelectric film placed between the optical components and the bandage layer 21. In the preferred embodiment, the sensing element is made from KYNAR film, a product of Atochem, Inc. The motion sensing element extends across the sensor head from one butterfly wing end 18 through and beyond the other end 11, into a tab 27 that, in the preferred embodiment, is disposed over the first joint of a finger, on the dorsal side, when the sensor is applied to the patient.

The change of strain on the motion sensing element (such as by bending the film strip) generates a charge within the element, as in a capacitor. A gain resistor mounted across the motion sensing element bleeds off the charge, thereby creating a voltage signal that is proportional to the rate of bending. The size of the gain resistor may be varied to permit differently dimensioned oximeter sensors (with differently dimensioned motion detection elements) to be used with the same oximeter. In the preferred embodiment, the gain resistor is mounted in the sensor connector.

An electrical cable 23 provides the LED driving current and returns photodetector 15 and motion sensing element 19 signals to the oximeter. In the preferred embodiment, the cable contains three shielded, twisted pairs of conductors, one pair each for the detector, the emitters and the motion sensing element. The cable's inner shield is coupled to the photodetector's Faraday shield. Both the outer and inner cable shields are tied to analog ground. All wires are terminated in the sensor connector.

In the preferred embodiment, an emitter coding resistor is included in the sensor connector. As is more fully explained in U.S. Pat. No. 4,621,643, the value of the coding resistor is related to the operating wavelengths of the emitters. The oximeter reads the value of this resistor to determine which coefficients to use in the saturation calculation.

In the preferred embodiment, the sensor connector is plugged into the front end of a custom preamplifier. The preamplifier may be external to the oximeter or incorporated within the oximeter.

Figure 3:
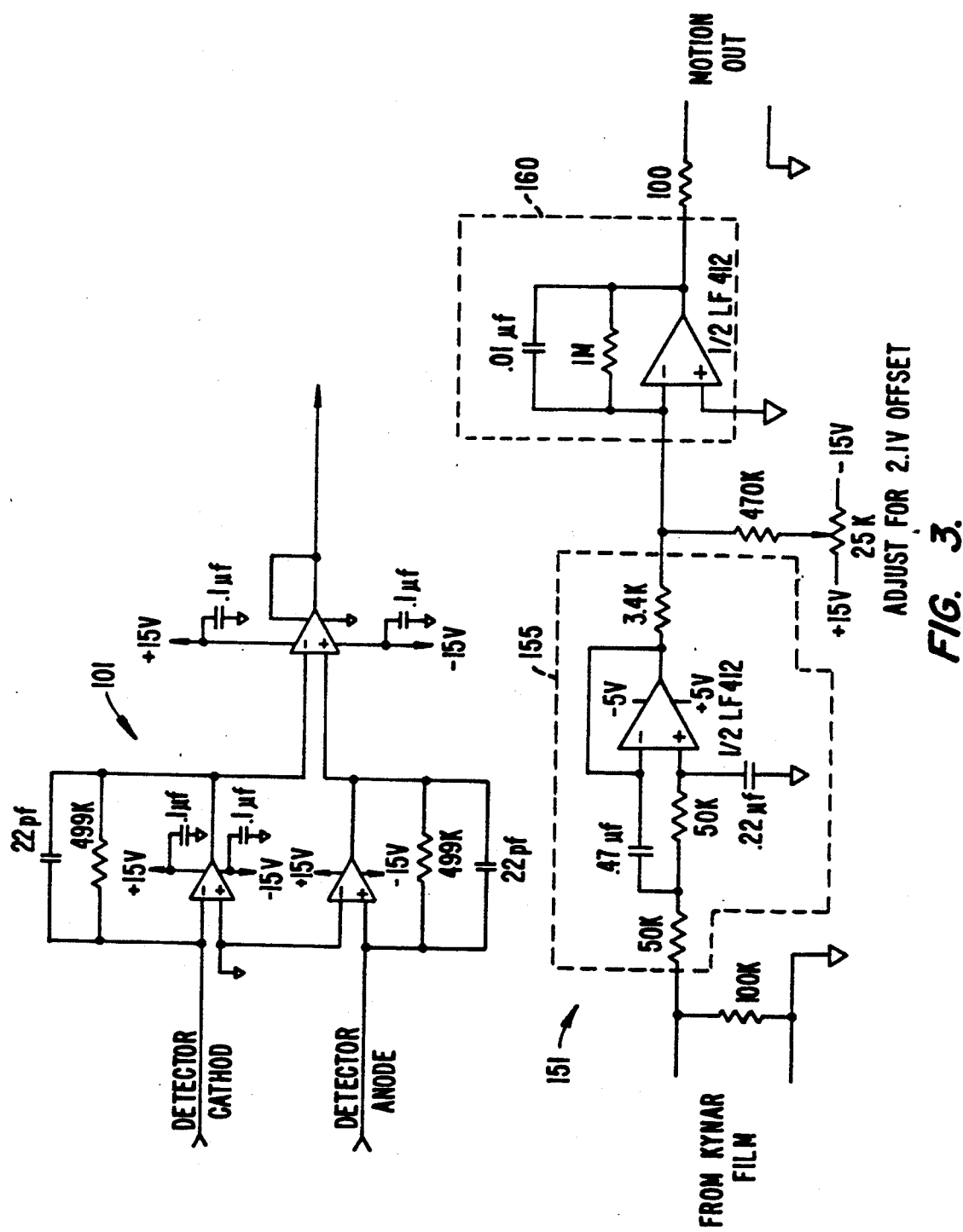
FIG. 3 is a schematic of the preamplifier used in the present invention.

As shown in FIG. 3 preamplifier 100 comprises a first section 101 to amplify the photodetector signal used to compute oxygen saturation and a second section 151 to condition the motion detector's output.

First section 101 comprises a differential input amplifier with an approximate gain of 1 million. This requires the sensor to be configured in a differential mode with shielded twisted pair conductors. No offset voltage is provided for dynamic range improvement but could be added. The output of the differential amplifier is transmitted to the pulse oximeter in known fashion.

As stated previously, KYNAR piezoelectric film element 19 can be modeled as a capacitor. When a strain is placed on the film, a charge is produced. The output of the film is proportional to the rate of change of the strain and it is A.C. coupled. To use this charge, a resistor 152 needs to be coupled in parallel with the film. The value of this resistor affects the voltage sensitivity of the film, which simply means that different sensor geometries need to be tuned with different resistors.

The voltage signal from the film/resistor combination is then passed through a unity gain, second order Butterworth filter 155 with a cut-off frequency of 10 Hz to reject line noise pickup. The band-limited signal is then amplified in amplifier 160 by a factor of 33,000 along with an inserted (adjustable) offset of 2.1 volts. The selection of the gain is arbitrary, based on obtaining "reasonable" output for typical motions. The offset was added to place the A.C. coupled output approximately in the middle of a 5 volt ADC input range.

In the preferred embodiment, the N-200 is modified to receive the conditioned motion signal through an unused channel of an ADC. The optical pulse signal is sampled at 57 hz, the ECG signal at 200 hz, and the motion signal at about 57 hz. The N-200 software is modified to read this additional ADC channel and process it along with the optical and ECG information. Collection of the optical and ECG signals is not changed.

Figure 4:
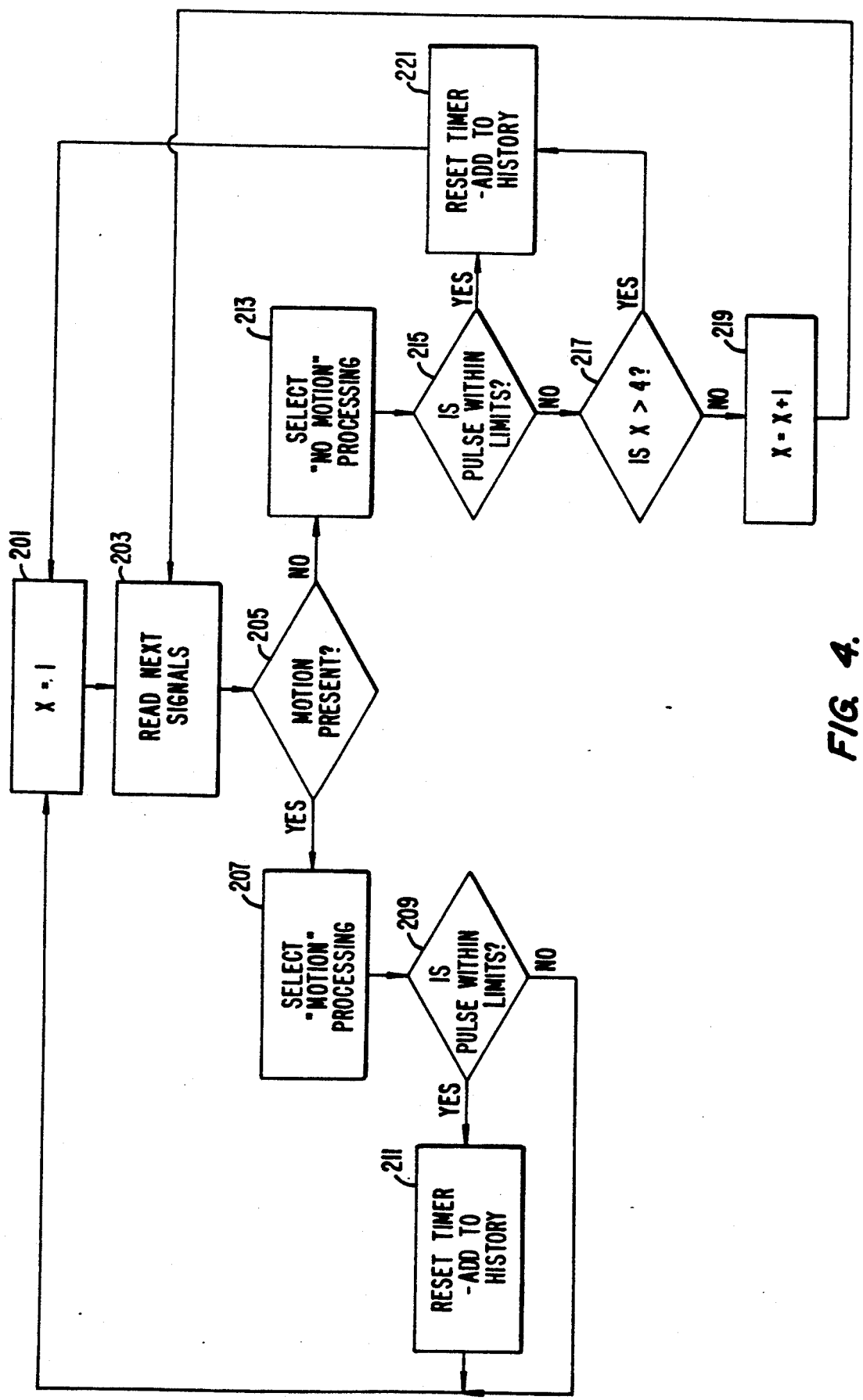
FIG. 4 is a flow chart showing how the present invention processes motion transient signals.

Referring now to FIG. 4, the oximeter detects the presence of motion by subtracting from the baseline signal of the motion signal at step 203, after it has been conditioned to remove background noise, taking the absolute value of the result and entering a "motion present" state at step 207 whenever the processed signal passes a fixed threshold as determined at step 205. In the preferred embodiment, the optimum threshold was determined empirically to be 1.22 millivolts. The oximeter leaves the "motion present" state 1.5 seconds after the processed signal falls below the threshold.

Entering a "motion present" state at step 207 changes the way the optical signals are processed and, therefore, the way blood oxygen saturation is calculated. Outside of the "motion present" state (step 213), the oximeter calculates blood oxygen saturation in any known appropriate manner. In the preferred embodiment, the oximeter maintains a history (step 221) consisting of the mean values over four consecutive pulses of three parameters as part of the saturation calculation algorithm: the period between successive optical minima, the IR optical pulse amplitudes, and the "ratio-of-ratios". The period and amplitude information is displayed by the oximeter. "Ratio of ratios" is used in the saturation calculation and is defined as follows:

$$\frac{Ln\frac{Red\ max}{Red\ min}}{Ln\frac{IR\ max}{IR\ min}}$$

Incoming pulses are checked against the history, and pulses are rejected if they are outside the permitted limits of variation (step 215). The first four pulses rejected for variation excess are not placed into the pulse histories (step 217 and 219). Once four pulses are rejected for this reason, subsequent pulses are placed into the history at step 221 to permit the history to reflect changing physiological conditions. If the pulse is accepted, a time-out clock is reset. The time-out clock normally sounds an alarm if no qualified pulse is detected within 15-20 seconds.

Before using the ratio-of-ratios in the saturation calculation, it is filtered as follows:

Filtered Ratio=unfiltered ratio *(N/256)+filtered ratio *(256−N)/256, where $1 \leq N \leq 255$ and N varies according to pulse rate and amplitude. For the first 5 pulses after locking onto the optical pulse, use N=255. After the first 5 pulses, calculate N for each pulse. The initial N varies depending upon the type and physiology of the patient. If locked on ECG, multiply the result by 3. If the rate is greater than 100, divide the result by 2. If the average IR amplitude is small, divide the result by 2. Filter the result against the previous result using a ½ old, ½ new filter. The final answer becomes the new N. Note that as N rises, the effective filtering decreases.

When the oximeter enters the "motion present" state (step 205), pulses which do not conform to the "history" accumulated prior to entering the "motion present" state are not accepted. This prevents the oximeter from mistakenly accepting false pulses caused by motion artifacts which pass other criterial checks employed by the oximeter after the first four bad pulses have gone by. Additionally, it prevents the oximeter from building up a history consisting of false pulses caused by motion artifact which would then prevent the N-200 from accepting good pulses once the motion artifact ceases.

Also, the oximeter uses a higher "N" value in the filtered ratio calculation for accepted pulses (step 207). This change permits the oximeter to use tighter filtering on data during the motion present state, while allowing the instrument to return its normal response time when motion is not present. Finally, the oximeter employs a 45 second pulse time-out period (step 207), as compared to the 15-20 second time out used when motion is not present (step 213) before triggering an alarm indicative of loss of pulse in the patient.

The foregoing description provides a full and complete disclosure of the preferred embodiments of the invention. Various modifications, alternate constructions, and equivalents may be employed without departing from the true spirit and scope of the invention. For example, although only the use of a piezoelectric film to provide motion detection has been described herein, other motion detection means such as accelerometers, or stain gauges could be substituted without changing the substance of this application. Therefore, the above description and illustrations should not be construed as limiting the scope of the invention which is defined by the appended claims.

What is claimed is:

1. A sensor for attaching to a patient for electro-optical measurement of at least one blood characteristic, comprising:
    optical signal means for generating a first electrical signal indicative of the at least one characteristic of the blood in a portion of the patient's tissue;
    a piezoelectric film;
    signal processing means, coupled to said piezoelectric film, for generating a second electrical signal indicative of movement in and of the portion of the patient's tissue; and
    means for transmitting the first and second electrical signal to an instrument for determining the blood characteristics.

2. The sensor of claim 1 wherein the signal processing means comprises an electrical impedance means coupled to the piezoelectric film.

3. The sensor of claim 1 wherein the signal processing means further comprises an electrical impedance means coupled to the piezoelectric film, the value of the electrical impedance means indicating the geometry of the piezoelectric film.

4. A system for measuring a blood characteristic of a patient comprising:
    a sensor comprising:
    optical means for generating a first electrical signal indicative of a characteristic of the blood in a portion of the patient's tissue;
    a piezoelectric film;

signal processing means, coupled to said piezoelectric film, for generating a second electrical signal indicative of movement in and of the portion of the patient's tissue; and means for transmitting the first and second electrical signals to an instrument for determining a blood characteristic;

means for receiving the first and second electrical signals from the sensor;

first processing means for operating on the second electrical signal for generating a signal indicative of motion; and second processing means for operating on the first electrical signal and the signal generated by the first processing means for determining a blood characteristic.

5. The system of claim 4 wherein the signal processing means comprises an electrical impedance means coupled to the piezoelectric film.

6. The system of claim 4 wherein the signal processing means further comprises an electrical impedance means coupled to the piezoelectric film, the value of the electrical impedance means indicating the geometry of the piezoelectric film.

* * * * *